United States Patent
Burton et al.

(10) Patent No.: US 6,703,488 B1
(45) Date of Patent: Mar. 9, 2004

(54) ANTIBODY/RECEPTOR TARGETING MOIETY FOR ENHANCED DELIVERY OF ARMED LIGAND

(75) Inventors: Jack D. Burton, Long Island City, NY (US); David M. Goldenberg, Mendham, NJ (US)

(73) Assignee: Center for Molecular Medicine and Immunology, Belleville, NJ (US)

( * ) Notice: Subject to any disclaimer, the term of this patent is extended or adjusted under 35 U.S.C. 154(b) by 464 days.

(21) Appl. No.: 09/231,642

(22) Filed: Jan. 15, 1999

Related U.S. Application Data

(60) Provisional application No. 60/071,520, filed on Jan. 15, 1998.

(51) Int. Cl.[7] .................................................. C07K 16/00
(52) U.S. Cl. .............................. 530/388.85; 530/387.1; 424/130.1; 424/156.1
(58) Field of Search .............................. 530/351, 387.1, 530/387.3, 388.8, 388.85; 424/85.1, 130.1, 133.1, 134.1, 136.1, 155.1, 156.1, 178.1; 435/7.1

(56) References Cited

U.S. PATENT DOCUMENTS 5,874,540 A * 2/1999 Hanson et al.

FOREIGN PATENT DOCUMENTS

| WO | 92/00762 | 1/1992 |
|---|---|---|
| WO | 93/19163 | 9/1993 |
| WO | 94/07535 | 4/1994 |
| WO | 94/22914 | 10/1994 |
| WO | WO 97/15663 | * 5/1997 |
| WO | 97/31946 | 9/1997 |
| WO | 98/16254 | 4/1998 |

OTHER PUBLICATIONS

MacLean et al.; "Anti–CD3:Anti–IL–2 Receptor–Bispecific mAb–Mediated Immunomodulation"; Journal of Immunology; vol. 155, No. 7; Oct. 1, 1995; pp. 3674–3682; XP002103531.

Seipelt et al.; "Overexpression, Purification, and Use of A Soluble Human Interleukin–4 Receptor α–chain/Igγ1 Fusion Protein for Ligand Binding Studies"; Biochemical and Biophysical Research Communications; vol. 239, No. 2; Oct. 20, 1997; pp. 534–542; XP002105430.

* cited by examiner

*Primary Examiner*—Larry R. Helms
(74) *Attorney, Agent, or Firm*—Foley & Lardner

(57) ABSTRACT

A method for intracellular delivery of drugs or other agents for diagnosis and therapy of malignancies or immune-mediated or inflammatory conditions. A targeting moiety of an antibody and the ligand-binding region of a selected cytokine receptor is used. The targeting moiety targets surface antigen on a specific cell population. The targeting moiety is administered to a subject, and then, after a specified interval, therapeutic or diagnostic agents linked to the cognate cytokine are given. The invention provides rapid, efficient internalization of the cytokine receptor antibody/antigen complexes. Targeting of a high-level cell surface antigen with such bispecific fusion molecules substantially increases the number of cytokine receptors over their low background level.

13 Claims, No Drawings

```
                           SEQUENCE LISTING

<160> NUMBER OF SEQ ID NOS:  1

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Linker

<400> SEQUENCE: 1

Gly Gly Ser Gly Ser Gly Gly Ser Gly Ser Gly Gly Ser Gly Ser
  1               5                  10                  15
```

ANTIBODY/RECEPTOR TARGETING MOIETY FOR ENHANCED DELIVERY OF ARMED LIGAND

This application claims the benefit under 35 U.S.C. §119(e) of U.S. Provisional Application No. 60/071,520, filed Jan. 15, 1998.

GOVERNMENT LICENSE RIGHTS

The U.S. Government has a paid-up license in this invention and the right in limited circumstances to require the patent owner to license others on reasonable terms as provided for by the terms of grant numbers CA 39841-13 and RR 12603, awarded by the National Institutes of Health.

BACKGROUND OF THE INVENTION

The present invention relates to a conjugate, preferably a fusion protein, of a component of an internalizing receptor complex and a monoclonal antibody (mAb) that binds to a specific surface antigen on a cell, to a conjugate of a radionuclide or toxin and a ligand for the internalizing receptor system, and to a method of diagnosis or therapy using such genetic or chemical conjugates.

There is now a fairly large and growing body of experience in the use of mAbs for tumor therapy. Several studies targeting different antigens have shown promising results. These studies have used radiolabeled mAbs and, to a lesser extent, mAb-toxin conjugates.

MAbs used in tumor diagnosis and therapy differ in their ability to bind cognate antigen and to become internalized. For example, CD22 exhibits efficient internalization as well as reexpression of this antigen after internalization. It suffers, however, from relatively low expression levels on some B-cell malignancies, e.g., it is expressed on only 30–50% of cases of B-cell lymphocytic leukemia (B-CLL).

Other cell surface antigens such as HLA-DR and the CD20 antigen, in contrast to the CD22 antigen, are quite highly expressed B-cell antigens that are expressed on a wide range of B-cell malignancies, ranging from acute lymphocytic leukemia (ALL) to the more differentiated B-Cell (B-CLL) and non-Hodgkin's lymphoma (NHL), and even to hairy cell leukemia (HCL). These antigens are generally expressed on cells in the vast majority of cases of these malignancies at a high antigen density. A major disadvantage of these antigens is that they are slowly internalizing. This feature militates significantly against targeting HLA-DR and CD20 for toxin-based therapy.

A further problem with HLA-DR and CD20 is the fact that B-cell malignancies exhibit a more rapid dissociation of bound anti-HLA-DR and anti-CD20 mAbs from the surface as compared to nonlymphoma tumor cells. This suggests that a therapy that targets a B-cell restricted antigen, particularly those characterized by slow internalization, could be enhanced by addressing these issues.

A variety of mAb-toxin constructs have been tested in both in vitro experiments and human trials. These studies have demonstrated potent and specific effects of these reagents. Most of the toxin molecules that have been used derive from either plant or bacterial sources and hence produce neutralizing anti-toxin antibody responses in patients. This severely limits the duration of therapy.

SUMMARY OF THE INVENTION

It is therefore an object of the present invention to provide more effective methods of diagnosis and/or therapy for cancer and immunologically-mediated or infectious diseases.

It is another object of the invention to improve the value as antigenic targets of slowly internalizing surface antigens.

It is a further object of the invention to reduce the tendency of antibodies bound to the surface of tumor cells to dissociate from the surface of the cells.

These and other objects of the invention are achieved by providing a targeting moiety comprising a conjugate of an antibody linked to a ligand-binding region of a receptor subunit selected from the group consisting of IL-2R$\alpha$, IL-4R$\alpha$, IL-13R$\alpha$ and IL-15R$\alpha$, which antibody is specific for a cellular antigen specific to a targeted cell. The targeting moiety may comprise a covalent conjugate in which the antibody is covalently linked to the ligand-binding region, a fusion protein of the antibody and the ligand-binding region, or a bispecific antibody that has a first specificity for a cellular antigen specific to a targeted cell and a second specificity for a rapidly internalizing receptor complex. In one embodiment, the antibody is specific to an antigen expressed by solid tumors, for example, CEA, and is linked to the ligand-binding region of IL-13R$\alpha$. In an alternative embodiment, the antibody is specific to HLA-DR and is linked to the ligand-binding region of IL-15R$\alpha$. A composition comprising a targeting moiety according to the invention and a pharmaceutically acceptable carrier also is provided.

A kit comprising a conjugate of IL-13 linked to a drug, radionuclide or toxin, and a targeting moiety comprising an antibody specific for a cell marker specific to a targeted cell, linked to the ligand-binding region of IL-13R$\alpha$, is provided. A second kit comprising a conjugate of IL-15 linked to a drug, radionuclide or toxin, and a targeting moiety comprising an antibody specific for a cell marker specific to a targeted cell, linked to the ligand-binding region of IL-15R$\alpha$, also is provided.

The invention provides a method of treatment for cancer, comprising first administering to a subject in need of such treatment a targeting moiety comprising an antibody specific for an antigen specific to a targeted cell, linked to the ligand-binding region of IL-13R$\alpha$, and then, after a predetermined time interval, administering to the subject a therapeutically effective amount of a conjugate of IL-13 linked to a drug, radionuclide or toxin. Another method of treatment for cancer or an immunologically-mediated or infectious disease comprises first administering to a subject in need of such treatment a targeting moiety comprising an antibody specific for an antigen specific to a targeted cell, linked to the ligand-binding region of IL-15R$\alpha$, and then administering to the subject a therapeutically effective amount of a conjugate of IL-15 linked to a drug, radionuclide or toxin.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

It has been discovered, surprisingly, that the value of surface antigens as antigenic targets can be improved significantly by functionally linking them to a high affinity, internalizing receptor system. The present invention is of particular advantage in the case of useful cell surface antigens that internalize slowly.

The present invention is based on a fundamental property of cytokine and growth factor receptors, viz., their ability to rapidly and efficiently internalize. Examples of rapid internalization of receptor and ligand include intracellular transport of nutrients, as with the transferrin and low-density lipoprotein (LDL) receptors. Receptors for growth factors like insulin and epidermal growth factor (EGF) as well as cytokine receptors such as IL-1R, IL-2R and IL-4R also internalize rapidly. In all cases studied, except that of transferrin, the ligand undergoes proteolysis as a consequence of trafficking to the low pH, protease/acid hydrolase-containing lysosomal compartment. Molecules associated with the ligands, such as cholesterol bound to LDL or drugs, toxins, and radionuclides, linked to other ligands can exit to extra-lysosomal compartments where they can exert their effects.

The fate of a receptor following internalization varies depending on the receptor system. For example, it may recycle to the cell surface, as with the transferrin and LDL receptors, or it may itself be degraded. Lysosomal degradation of receptors has been reported for receptors such as the EGF receptor and contributes to receptor down-regulation and desensitization to subsequent ligand stimulation.

In some ligand/receptor systems, there is re-expression of receptors via de novo mRNA and protein synthesis. For example, CD22 is internalized rapidly after binding of the cognate LL2 mAb and is re-expressed as soon as 2 hours after a complete cycle of antigen saturation binding of cognate antigen by the specific mAb followed by internalization at 37° C. Further evidence of re-expression is found in the ability of a wide array of cytokine/growth factor-dependent cell lines to be maintained for months or even years, suggesting ongoing re-synthesis and re-expression of the requisite ligand binding as well as the associated signaling proteins. Taken together, these observations show that cytokine receptors are capable of multiple, rapid cycles of internalization and re-expression and hence have a high capacity for intracellular delivery of ligands.

In accordance with the present invention, it is possible to induce rapid internalization of a slowly internalizing antigen by bringing it in juxtaposition with a more rapidly internalizing complex. For example, the IL-2 receptor system consists of an alpha (IL-2Rα, formerly Tac antigen) beta (IL-2Rβ) and gamma ($\gamma_c$) chain. IL-2Rα internalizes slowly, but once it becomes physically associated with IL-2Rβ and $\gamma_c$ by the presence of the IL-2 ligand the entire trimeric protein complex becomes internalized at the rapid intrinsic rate of the IL-2Rβ/$\gamma_c$ dimer. This follows a recurring pattern in cytokine biochemistry, in which a functional receptor consists of two or more subunits, one of which is typically a private, specific alpha chain. The IL-6-IL-6R system is particularly notable in that the extracellular domain of the alpha subunit has an intrinsic ability to associate with the gp130 signaling molecule such that, when IL-6 plus a soluble form of IL-6Rα are added to cells that express only gp130, a signaling response occurs. The IL-2 and IL-6 receptor systems are exemplary of two major cytokine signaling subunits, $\gamma_c$ (utilized by receptor complexes for ILs-2, 4, 7, 9 and 15) and gp130 (utilized by receptor complexes for ILs-6 and 11, CNTF, LIF, OSM and cardiotrophin-1), respectively.

Receptor systems can be harnessed according to the present invention to provide enhanced intracellular delivery of armed ligands. Cytokine receptors can be targeted to the surface of cells that normally lack such receptors by the use of mAb-receptor conjugates. For example, the alpha chains of the IL-6 and the ciliary neurotrophic factor (CNTF) receptors have been targeted to the surface of previously negative cells by way of mAbs directed against the CD34, CD45 and CD64 cell surface antigens. Addition of such mAb-Rα conjugates to factor-dependent cells conferred de novo, specific responsiveness to IL-6 or CNTF.

A targeting moiety according to the invention comprises a receptor linked to a MAb fragment up to F(ab')$_2$ size. Suitable antibody fragments include F(ab')$_2$, F(ab)$_2$, Fab', Fab, Fv and the like, including hybrid fragments. Also useful are any subfragments that retain the hypervariable, antigen-binding region of an immunoglobulin. This will include genetically engineered and/or recombinant proteins, whether single-chain or multiple-chain, which incorporate an antigen binding site and otherwise function in vivo as targeting vehicles in substantially the same way as natural immunoglobulin fragments. Single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole Ig. The fragments may also be produced by genetic engineering. When the term "antibody" is used herein, all the above types of fragments are included therein.

MAb fragments such as the single chain antibody scF$_v$, have the added advantages of rapid blood and organ clearance and improved penetration into tumor nodules and, in a preferred embodiment, scF$_v$ of a MAb to a desired target antigen is linked to the ligand-binding region of a receptor. MAb molecular engineering techniques can be used to produce scF$_v$. This molecule can be produced by cloning the V$_H$ and V$_L$ segments from the mAb of interest and splicing them together with a short linker region interposed between them. These molecules, after proper design and renaturation, retain the antigen binding activity of the parent mAb and can be expressed at high levels in *E. coli*-based insect or mammalian expression systems. These constructs then can provide a platform for the engineering of bifunctional single chain molecules that can link a second moiety (receptor or a second single chain antibody) to the first to retarget effector cells or molecules.

Mixtures of antibodies, as well as hybrid antibodies, can be used. The hybrids can have two specificities, e.g., one arm binding to one antigen on the target cell and another arm binding to another antigen on the target, or one arm could possess a ligand binding region of a receptor subunit. Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. No. 4,479,895, U.S. Pat. No. 4,474,893, U.S. Pat. No. 4,714,681, and in Milstein et al., *Immunol*. Today 5:299 (1984), all incorporated herein by reference. The foregoing are merely illustrative, and other combinations of specificities can be envisioned that also fall within the scope of the invention.

The antibody is linked to the extracellular domain of a receptor. Since the entire extracellular domain is large, truncated versions of the domain that contain the ligand-binding site can be used. The antibody/receptor conjugate can be formed by covalently linking the antibody to the receptor, directly or through a short or long linker moiety, through one or more functional groups on the antibody and/or the enzyme, e.g., amine, carboxyl, phenolic, thiol or hydroxyl groups, to form a covalent conjugate. Various conventional linkers can be used, e.g., diisocyanates, diisothiocyanates, bis(hydroxysuccinimide) esters, carbodiimides, bismaleimides, dithiols, maleimide-hydroxysuccinimide esters, glutaraldehyde and the like. The antibody construct may bind one arm to either the ligand binding region or a site that is remote from the ligand-binding site depending on whether ligand will be employed in a given application.

A simple method is to mix the antibody with the ligand-binding region in the presence of glutaraldehyde to form the antibody/receptor conjugate. The initial Schiff base linkages can be stabilized, e.g., by borohydride reduction to secondary amines. This method is conventionally used to prepare, e.g., peroxidase-antibody conjugates for immunohistochemical uses or for immunoassays. A diisothiocyanate, a bishydroxysuccinimide ester, carbodiimide or other bifunctional crosslinkers can be used in place of glutaraldehyde.

More selective linkage can be achieved by using a heterobifunctional linker such as a maleimide-hydroxysuccinimide ester. Reaction of the latter with an the ligand-binding region of the receptor will derivatize amine groups on the receptor, and the derivative can then be reacted with, e.g., an antibody Fab fragment with free sulfhydryl groups (or a larger fragment with sulfhydryl groups appended thereto by, e.g., Traut's Reagent).

It is advantageous to link the ligand-binding region of the receptor subunit to a site on the antibody remote from the antigen binding site. This can be accomplished by, e.g., linkage to cleaved interchain sulfhydryl groups, as noted above. Another method involves reacting an antibody whose carbohydrate portion has been oxidized, with a ligand-binding region which has at least one free primary amino group. This results in an initial Schiff base (imine) linkage, which is preferably stabilized by reduction to a secondary amine, e.g., by borohydride reduction, to form the final conjugate.

Alternatively, the antibody/receptor conjugate comprises a bispecific antibody conjugate which is linked immunologically to the ligand-binding region of a receptor. The bispecific antibody or antibody fragment has a first specificity for a cellular antigen specific to a targeted cell and a second specificity for an extracellular region of the ligand-binding subunit or another subunit of the receptor complex.

Most preferably, the antibody/receptor conjugate comprises a fusion protein, in which a fusion sequence comprising antibody linked to a ligand-binding region of the receptor is expressed in a recombinant, virion-based, mammalian expression system or other mammalian, insect, yeast or *E. coli*-based expression system. Suitable linkers for linking the antibody to the ligand-binding region are, for example, $(GGSGS)_3$ or (SEQ ID NO: 1) the 23-amino acid linker disclosed in Kurucz et al., *J. Immunol.* 154: 4576–4582 (1995).

Any of the antibody/receptor conjugates can be labeled directly with, or conjugated or adapted for conjugation to, a radioisotope or magnetic resonance image enhancing agent. In a preferred embodiment, the antibody/receptor bifunctional construct is unlabeled. It is administered and then, after a predetermined interval sufficient for localization to the target site and also clearance from the circulatory system of the mammal, the armed cognate ligand will be given. This is particularly important when boron complexes are used therapeutically. Alternatively, the conjugate is tagged with a label, e.g., a radiolabel, a fluorescent label or the like, that permits its detection and quantitation in body fluids, e.g., blood and urine, so that targeting and/or clearance can be measured and/or inferred.

Any conventional method of radiolabeling, which is suitable for labeling proteins for in vivo use, generally is suitable for labeling these antibody/receptor conjugates. This can be achieved by direct labeling with, e.g., I-131, I-124 or I-123. Labeling with either I-131, I-124 or I-123, is readily effected using an oxidative procedure wherein a mixture of radioactive potassium or sodium iodide and the antibody is treated with chloramine-T, e.g., as reported by Greenwood et al., *Biochem. J.*, 89: 114 (1963) and modified by McConahey et al., *Int. Arch. Allergy Appl. Immunol.*, 29: 185 (1969). This results in direct substitution of iodine atoms for hydrogen atoms on the antibody molecule, presumably mostly on tyrosine residues, possibly also on tryptophan and even on phenylalanine residues, depending on the proportions of reagents and the reaction conditions. Alternatively, either Iodogen-based methods, as described by Fraker et al., Biochem Biophys Res. Commun 80:849–857, 1978, or lactoperoxidase iodination may be used, as described by Feteanu, supra, page 303, and references cited therein.

Instead of I-131, I-124 or I-123, the conjugate can be labeled by metallation with, e.g., Tc-99m or Cu ions or the like, by conventional techniques, or by attaching a chelator for a radiometal or paramagnetic ion. Such chelators and their modes of attachment to antibodies are well known to the skilled artisan.

The antibody/receptor conjugate acts as a targeting moiety according to the invention when administered to a patient. This is followed by a targeting and clearance interval that allows for binding of the targeting moiety to intended target cells and its clearance from normal tissues, after which armed ligand is administered. The armed ligand comprises the cognate ligand for the receptor of the targeting moiety, conjugated to a radionuclide, drug or toxin. The radionuclide can be either a diagnostic or therapeutic radionuclide.

Examples of diagnostic radionuclides include iodine-123, iodine-124, iodine-131, indium-111, gallium-67, gallium-68, ruthenium-97, technetium-94, technetium-99m, copper-64, copper-67, cobalt-57, cobalt-58, chromium-51, iron-59, yttrium-86, selenium-75, thallium-201, and ytterbium-169. Examples of therapeutic radionuclides include alpha-emitters, e.g., bismuth-212 and astatine-211; beta-emitters, e.g., yttrium-90, rhenium-186, rhenium-188, copper-67 and iodine-131; and alternatively, electron capture or Auger conversion electron-emitting radionuclides such as iodine-125, indium-111 and gallium 67. Preferably the radionuclide will emit in the 10–5000 keV range, more preferably in the 50–1500 keV range, and most preferably in the 50–500 keV range. The radionuclides may be incorporated into the specific antibody by the labeling techniques discussed above, as well as other conventional techniques well known to the art.

Many drugs and toxins are known which have a cytotoxic effect on tumor cells or microorganisms that may afflict humans and mammals in general. They are to be found in compendia of drugs and toxins, such as the Merck Index and the like. A preferred toxin is a ribonuclease, such as onconase. Onconase is a non-mammalian RNAse purified from *Rana pipiens* oocytes. It has been shown in clinical trials to have anti-tumor activity against human pancreatic cancer, but has been found to have minimal anti-tumor activity against B-cell malignancies such as B-cell lymphoma or leukemia.

Addition of the armed ligand (specifically IL-2 or IL-15) results in the formation of a trimeric complex comprising the β/γ$_c$ chain subunits present on the surface of the targeted cell and the α-chain subunit of receptor, which is attached to the surface of the targeted cell by means of the antibody/receptor conjugate. This leads to rapid internalization of toxin and/or radionuclide into the targeted cells. An analogous dimeric or trimeric complex assembles after the addition of IL-4 or IL-13. While internalization is not necessary for a therapeutic radionuclide to be effective, these multimeric complexes provide a tighter, more stable binding of ligand to the targeted cells, and also facilitates internalizations.

The same ligand can be armed with both radionuclide, drug and toxin, or separate ligands can be armed with radionuclide, drug and toxin. Where separate ligands armed with radionuclide, drug and toxin are used, these may be administered together or sequentially.

The antibody/receptor conjugate and armed ligand conjugate are administered in a composition with a pharmaceutically acceptable carrier. In this regard, a pharmaceutically acceptable carrier is a material that can be used as a vehicle for administering the fusion protein or armed ligand because the material is inert or otherwise medically acceptable, as well as compatible with the fusion protein or armed ligand.

Preferred high affinity, internalizing receptor systems to which the antibody can be linked include the IL-2, IL-4, IL-13 and IL-15 receptor systems. Internalization rates for IL-2/IL-2R (related to the IL-15/IL-15R system) and for IL-4/IL-4R (related to the IL-13/IL-13R system) have $t_{1/2}$ values of approximately 15–30 minutes. Particularly preferred receptor systems for use in the present invention are the IL-13 and IL-15 receptor systems.

The IL-13/IL-13 receptor system is a good candidate for addressing solid tumors due to its widespread expression and signaling capability on cancers of epithelial origin (preponderantly CEA+, as well as important CEA-epithelial cancers such as renal cell carcinoma). The IL-13/IL-13 receptor system shares several features in common with the IL-4/IL-4 receptor system. Structurally, the IL-4 and IL-13 ligands show approximately 30% protein sequence homology, which is the highest amongst the interleukins. Both receptors possess the canonical four conserved cysteine residues in the N-terminal half of their extracellular domains as well as a WSXWS motif in the juxtamembrane region of their extracellular domains, and are members of the hematopoietin superfamily. IL-13Rα is of smaller overall size than IL-4Rα, but has a somewhat larger extracellular domain and a correspondingly shorter intracellular domain.

IL-13 and IL-4 have considerable functional similarity as well. Both suppress production of pro-inflammatory cytokines by macrophages, are co-stimulatory for B cell proliferation and induce immunoglobulin isotype switching. Both induce upregulation of both CD23 and MHC class II on both monocytes and B cells. IL-13 and IL-4 bind nonhematopoietic cells, such as carcinoma cell lines, with high affinity and exert biologic effects on them. IL-4 inhibits the growth of these epithelial cancer cell lines both in unmodified form both in vitro and in vivo. Unmodified IL-13 also has in vitro growth-inhibitory effects on breast carcinoma cell lines, and thus shares this property.

In several cell types, IL-13 competes for IL-4 binding and vice versa, indicating that IL-4 and IL-13 share receptor components. In addition, a mutant form of IL-4, Y124D, is capable of inhibiting both IL-4 and IL-13 biologic responses in lymphoid and nonlymphoid cell types. The nonlymphoid cell types are predominantly negative for γ$_c$, while all of these cell types express varying amounts of IL-13Rα and IL-4Rα. Both IL-4Rα and IL-13Rα, when expressed alone, bind their cognate ligands with a similar high affinity, with $K_aS$ of approximately $10^{10}$ M$^{-1}$. The soluble form of IL-4Rα has been shown to retain this ligand-binding ability. Soluble forms of IL-13Rα have recently been shown to retain ligand-binding ability both in vitro and in vivo. When IL-4Rα and IL-13Rα are coexpressed, they are capable of forming a complex that can be impacted by both ligands as well as antagonistic ligands like IL-4-Y124D.

Human IL-13Rα is expressed at either low or moderate levels at both the mRNA and protein level by a variety of hematopoietic and epithelial cell lines. In colon carcinoma cells, specific signaling events, namely, Jak 2 tyrosine kinase activation, have been shown to occur in conjunction with IL-4's biologic effects.

The cytotoxic activity exhibited by IL-4-Pseudomonas exotoxin (IL-4-PE) and IL-13-PE fusion molecules provides further evidence of the efficient internalization of these receptor systems, since a wide range of carcinoma cell lines are quite sensitive to these cytotoxins. Several different IL-4-PE constructs have been made that are active in vitro and in a mouse xenograft model, and analogous IL-13-PE constructs have been shown to possess equally potent in vitro activity. Likewise, diphtheria-IL-4 fusion proteins (e.g. $DAB_{389}IL-4$) exhibit in vitro cytotoxic activity.

IL-13's effects are comparable to IL-4, both in unmodified form and linked to PE. However, unmodified IL-13 can be given at higher doses than IL-4 and IL-13-PE shows less toxicity towards hematopoietic cells than IL-4-PE. Epithelial cancer cell lines can be targeted and killed by IL-13-toxins as readily as by corresponding IL-4-toxins, indicating that the IL-13 receptor complex internalizes as efficiently as the IL-4 receptor complex. Unlike IL-4, IL-13 has no biologic effect on T cells. For these reasons, the IL-13 receptor system is preferred to the IL-4 receptor system for diagnostic and therapeutic use in vivo.

In a preferred embodiment, the IL-13 receptor system is used in conjunction with a functional antibody, preferably a single chain mAb (scF$_v$), to carcinoembryonic antigen (CEA). CEA represents an attractive antigenic target for several reasons. It is a tumor-associated antigen that it is absent or poorly expressed by normal tissues and highly expressed by the vast majority of carcinomas of colon, lung, breast, pancreatic, gastric, ovarian, and medullary thyroid origin. High incidence and mortality rates for these cancers coupled with suboptimal diagnostic and therapeutic options result in a serious and persistent overall public health problem.

CEA is a glycosylated cell surface protein of approximately 180 kDa, and is a solid tumor antigen that has been extensively studied clinically, both as a circulating tumor marker and as an antigenic target for radiolabeled mAbs for imaging and therapy. A number of anti-CEA antibodies have been under study in phase I–III clinical diagnostic and therapeutic trials. Exemplary of an anti-CEA mAb is the MN-14mAb. A humanized version of this mAb, hMN-14, in which human constant and framework regions replace the corresponding mouse sequences, has been constructed and expressed and is the mAb and used in these clinical trials. A $^{99m}$Tc-labeled Fab' fragment of another, related anti-CEA mAb, Immu-4, has received FDA approval for the detection and staging of colon cancer.

Though promising as an imaging agent, radiolabeled anti-CEA mAbs in the therapeutic mode previously have yielded few responses. A low response rate resulted even when an anti-CEA mAb was co-administered with an anti- TAG-72 mAb, recognizing a second, distinct highly expressed tumor-associated antigen, along with IFN-α, which upregulates both antigens, on a group of patients with metastatic colon cancer. Advanced colon cancer likewise has been quite resistant to all chemotherapeutic combinations tested to date.

The present invention seeks to overcome these therapeutic barriers, which are common to most solid tumors, by enhancing the internalization of CEA. An anti-CEA targeting moiety, such as shIL-13Rα-anti-CEA scF$_v$ fusion protein, is administered to a subject and, after the targeting moiety localizes at the tumor sites, IL-13 ligand armed with a therapeutic or diagnostic moiety is delivered. This system provides diagnostic and therapeutic options for the large number of CEA+ malignancies, including cancers of the lung, colon, breast, stomach, ovary and pancreas, most of which express both CEA and IL-13 receptor components. The IL-13 receptor components enable rapid internalization of the armed ligand, to selectively deliver high levels of cytotoxic agents to a large group of tumors. Targeting a highly expressed antigen, such as CEA, with a sIL-13Rα-anti-CEA scF$_v$ fusion molecule, increases the typically low number of cytokine receptors by up to two orders of magnitude.

The IL-15/IL-15 receptor system is a good candidate for targeting B-cell and T-cell malignancies, normal or activated B cells, and activated T cells. The IL-15/IL-15 receptor system shares several features in common with the IL-2/IL-2 receptor system. In vitro and in vivo, both IL-2Rα and IL-4Rα have soluble forms, which bind cognate ligand. The IL-2/IL-2 receptor system has a trimeric receptor. IL-15, like IL-2, uses IL-2Rβ and γ$_c$, but not IL-2Rα (formerly Tac). The specific alpha chain of IL-15 (IL-15Rα) has homology and a similar structural organization to IL-2Rα. While IL-15Rα is homologous structurally to IL-2Rα, it has a significantly higher affinity for its cognate ligand, with a K$_a$ of ~$10^{10}$ M$^{-1}$)

IL-2Rα expressed in the absence of the other two chains internalizes slowly, but when juxtaposed to the other subunits by the presence of ligand, the entire ligand/αβγ complex internalizes at the rapid rate intrinsic to the IL-2Rβ/γ$_c$ dimer (t$_{1/2}$ of approximately 15 minutes). By comparison IL-15Rα has an affinity for its cognate ligand (K$_a \geq 10^{10}$ M$^{-1}$) that is at least two orders of magnitude greater than that of IL-2Rα for IL-2.

T, B, NK and monocyte populations respond to IL-15 and correspondingly are positive for IL-2Rβ/γ$_c$ +/−IL-15Rα. In addition, B-lymphoma/leukemia expresses IL-2Rβ, while γ$_c$ is nearly uniformly expressed by all normal and malignant hematopoietic cells. The minimal functional receptor structure for IL-2 and IL-15 requires co-expression of IL-2Rβ and γ$_c$. Therefore, both normal leukocyte populations, which may be pathogenic and which have been targeted in immune/inflammatory conditions, as well as the malignant counterparts of B-cells and T-cells can be targeted according to the invention. While similar in many respects, the IL-15 receptor system provides at least one advantage over the IL-2 receptor system, having somewhat less capacity to induce clinically apparent vascular permeability.

In a preferred embodiment, the IL-2 or IL-15 receptor system is used in conjunction with a functional single chain mAb (scF$_v$) to HLA-DR. HLA-DR is a favorable antigenic target. It is expressed by a range of hematopoietic malignancies (particularly, B-lymphomas and B-leukemias) as well as certain normal immune cells, such as B cells, monocytes, dendritic and activated T cells. Like CEA, it is expressed at levels that can reach $10^6$ sites/cell, and it is internalized at a slow rate.

The absence of HLA-DR antigen from many critical normal cell populations, such as pluripotent bone marrow stem cells, adds to its clinical utility. This undifferentiated stem cell population can replenish any depletions in differentiated normal cell populations, as has been observed in myelotoxic situations such as cancer chemotherapy and bone marrow transplantation. Moreover, in certain severe cases of immune-mediated disease, these cell populations may need to be eliminated or significantly attenuated.

There is a large body of clinical experience in the treatment of B-cell malignancies with mAbs directed against HLA-DR (using the Lym-1 mAb), as well as other B-cell-specific mAbs, including CDs19–22 and CD37. In these studies, radiolabeled mAbs or mAbs linked to toxin have been used therapeutically against malignant B cells. Immunotoxins also have been employed to eliminate pathogenic T cells in unrelated-donor bone marrow transplantation.

Effective and selective cellular cytotoxicity via the IL-15 receptor and single chain mAb (scF$_v$) to HLA-DR according to the invention yields significant clinical benefits in a wide range of cancers, including B-cell lymphomas and leukemias, as well as many immune-mediated diseases including autoimmune and inflammatory diseases such as autoimmune diabetic states, inflammatory bowel disease, systemic lupus erythematosus, rheumatoid arthritis, and severe psoriasis, and allograft reactions such as organ transplant rejection and graft-versus-host disease in bone marrow transplantation. Specific targeting of highly expressed HLA-DR antigen on an activated T cell population with an sIL-15Rα-anti-HLA-DR scF$_v$ targeting moiety achieves more specificity and effectiveness in eliminating reactive T cell populations.

In accordance with the invention, an anti-HLA-DR targeting moiety, for example, a shIL-15Rα-anti-HLA-DR scF$_v$ fusion protein such as sIL-15Rα-Lym-2 scF$_v$, is administered to a subject. After the targeting moiety localizes at the therapy site, IL-15 ligand armed with a therapeutic or diagnostic moiety is delivered. The IL-15 receptor is predicted to enhance the internalization of HLA-DR, to selectively deliver high levels of cytotoxic agents. Here again, MAb fragments such as scF$_v$ can be used to provide the added advantages of rapid blood and organ clearance. By careful selection of components, delivery systems with minimal immunogenicity can be achieved. The armed ligand, the R-α moiety and the mAb scF$_v$ can be tailored to fit the characteristics of the particular disease.

The present invention is designed to provide higher tumor/non-tumor ratios, as can be achieved with traditional pretargeting systems that utilize avidin or streptavidin and biotin, while eliminating certain problems associated with these systems. While the avidin-biotin system has a very high affinity, clinical experience has shown that approximately 20–30% of patients mount an antibody response against avidin and up to 70% make antibodies to streptavidin. The present invention avoids the immunogenicity of avidin and biotin. A three-step approach can be implemented by using an anti-idiotypic mAb, WI2, that is reactive to the antigen combining site of MN-14, and thereby any humanized version of MN-14. The WI2 mAbs have been galactosylated, which allows for rapid blood clearance of unlabeled MN-14-based reagent through the hepatic asialoglycoprotein receptor. These pretargeting approaches strive for maximal blood and organ clearance of the first step unlabeled pretargeting agent prior to administering the armed second or third step reagent, in order to minimize normal tissues' exposure to armed diagnostic or therapeutic agents and to maximize tumor/normal tissue ratios of the armed agent.

In sum, the present invention approach offers potentially beneficial alternatives to current approaches for several reasons. First, it uses agents with decreased immunogenicity. MAb fragments have inherently lower immunogenicity, particularly hMN-14mAb which has been humanized. The receptor and ligand components are native and non-immunogenic. Second, the invention uses a pretargeting strategy that permits higher specific delivery of armed ligand to tumor sites or pathogenic cell populations. Third, the invention maximizes internalization of ligand to allow higher intracellular concentration of armed ligand and better diagnostic or therapeutic effects. Fourth, the invention allows a therapeutic approach with combinations or sequences with various agents including drugs, toxins, radionuclides, antisense and antigene reagents. To accomplish this, different armed forms of the same ligand are used. Finally, the present invention uses cytokines which appear favorable in their toxicity profiles and can be applied to a wide range of diseases.

The following examples are illustrative of the present invention, but are not to be construed as limiting.

EXAMPLE 1

Construction of a Bifunctional Soluble IL-13Rα-MN-14scF$_v$ Fusion Protein

An MN-14scF$_v$ was produced by PCR amplification of cDNA from the humanized MN-14transfectoma. The linker used for MN-14scF$_v$ was a 15-amino acid linker (GGSGS)$_3$ and the orientation was V$_L$-linker-V$_H$. After confirmation of the DNA sequences, the single chain construct was subcloned into an appropriately restricted containing expression plasmid used for other scF$_v$s. This construct then was subcloned into BL21(λDE3) E. coli for expression.

The protein was solubilized and renatured from inclusion bodies and was purified by sequential anion exchange and gel filtration chromatography. After functional evaluation, the scF$_v$ fragment was ligated to a DNA fragment encoding PE40. This immunotoxin was shown to have specific cytotoxicity for CEA+ cell lines.

Another single chain construct also was made. This was made with the opposite 5'–3' orientation of the heavy and light chains, was assembled in pCANTABE5E (Pharmacia Biotech, Piscataway, N.J.) and expressed in phage. Specific binding of recombinant phage expressing this scF$_v$ was demonstrated by ELISA.

The V$_L$-linker-V$_H$ sequence is used for construction of the IL-13Rα-MN-14fusion protein, as diagrammed below. A 23-amino acid linker is used between shIL-13Rα and the scF$_v$, as per Kurucz et al. (1995). Alternatively, the (GGSGS)$_3$ (SEQ ID NO: 1) linker which was used in construction of the MN-14scF$_v$ described above is used. The configuration of this fusion protein is:

shIL-s13Rα-linker—V$_L$—(GGSGS)$_3$—V$_H$

The DNA fragment encoding the soluble, extracellular domain of IL-13Rα is obtained by PCR amplification from positive cell lines, currently Caki-1, HuT 102B2 and A549. PCR primer pairs for RT-PCR are synthesized, including a primer pair for cloning. The primer pairs span almost the entire extracellular domain of the receptor.

The primers include unique restriction enzyme sites to allow for directional cloning into the expression vector, pSinrep 5. This vector is part of a high-level Sindbis virus-based, mammalian expression system (Invitrogen, San Diego, Calif.). The recombinant plasmid will include the wild-type signal sequence and hence can be secreted into the cell culture medium. The ligand-binding region is predicted to lie in the N-terminal half of the molecule, a considerable distance away from the scF$_v$ domains, and thus the above configuration was selected. To allow unhindered folding of individual domains a 23-amino acid linker is included, as has been described for a bispecific single chain protein, i.e., a fusion of two scF$_v$s.

In order to retain sequences potentially important for interactions of IL-13R with partner proteins such as IL-4R, it is preferable to retain the WSXWS domain and all of the conserved cysteine residues, along with nearly all of the extracellular domain. This maximizes the possibility of interaction with associated proteins in the membrane, thereby facilitating the binding and internalization of the IL-13/IL-13 receptor complex.

EXAMPLE 2

Expression and Purification of the Bifunctional Soluble IL-13Rα-MN-14scF$_v$ Fusion Protein Bacterial clones containing recombinant pSinRep5 plasmids are screened and those with correct sequences are used for expression. Recombinant virions are produced to provide higher expression and a stable reusable stock for multiple transductions. This is accomplsihed by co-transfection of in vitro transcribed RNA from the recombinant plasmid plus a replication-deficient helper virus DNA template (as per manufacturer's instructions). Alternatively, an E. coli-based expression system, similar to the one used for production of MN-14scF$_v$ is used.

When recombinant Sindbis virions are used, RNA transcription is performed from the recombinant plasmid (prepared from the initial pSinRep5 plasmids) and a helper virus plasmid that is included in a standard kit. (Invitrogen, Inc., San Diego, Calif.) RNA yields are assessed by agarose gel electrophoresis and the RNAs then are used to co-transfect the BHK cell line. This is done using cationic liposomes and/or electroporation. After 3 days in culture the supernatant from the transfection is collected and used to transduce fresh BHK cells to assess viral titer and to assess the level of recombinant protein expression. For all transductions, cells are plated initially in FCS-containing medium. After approximately 20 hours, the medium is changed to serum-free medium. After 3 days, supernatants from recombinant and non-recombinant controls are collected and aliquots are concentrated by centrifugal ultrafiltration for total protein determination (Coomassie plus™, Pierce, Rockford, Ill.).

Aliquots of the concentrated supernatant are fractionated by SDS-PAGE. The gel is divided for Coomassie staining and electroblotting onto PVDF for Western blotting. sIL- 13Rα-MN-14scF$_v$ expression is detected with goat anti-human IgG-peroxidase to detect hMN-14sequences and development by chemiluminescence. After exposure to photographic film, the blot is examined for a specifically stained band of approximately 70 kDa.

Once expression is confirmed the transductions are scaled up. For large-scale expression runs, the purification scheme includes anion exchange, gel filtration and/or other HPLC modes with determination of final recovery and purity. In initial genetic constructs a C-terminal hexahistidine or related inert affinity tag sequence will be added to assist purification.

EXAMPLE 3

Assay of Antigen and Ligand Binding Activity of Soluble IL-13Rα-MN-14scF$_v$ Fusion Protein Purified sIL-13Rα-MN-14scF$_v$ is $^{125}$I-labeled by the Iodogen (Pierce) method to approximately 5–10 μCi/μg. The LS174T cell line is used for binding studies since it expresses high levels of CEA and has low to moderate IL-13 binding.

An amount of 1×10$^6$ washed LS174T cells/tube is suspended in 100 μl of binding buffer (RPMI 1640/10% FCS). Either labeled sIL-13Rα-MN-14scF$_v$ at 10 nM alone or labeled sIL-13Rα-MN-14scF$_v$ at 10 nM together with a 200 fold molar excess of the unlabeled protein is added to replicate tubes. The overall ability to bind antigen is assessed by using tracer concentrations (50–200 pM) of labeled fusion protein and larger numbers of LS174T cells. The bindable fraction should be greater than 50% in antigen excess.

IL-13 binding ability is assessed using $^{125}$I-IL-13 (Iodogen labeled as before). To replicate tubes containing 1×10$^6$ LS174T cells is added either unlabeled fusion protein or buffer. After 30–40 min at 4° C. cells are washed and $^{125}$I-IL-13 is added, either in the presence or absence of cold IL-13. A significant positive increment in specific IL-13 binding indicates a functional IL-13Rα moiety.

EXAMPLE 4

Assay of Ability of Soluble IL-13Rα-MN-14scF$_v$ Fusion Protein to Internalize CEA sIL-13Rα-MN-14scF$_v$ is radioiodinated to a specific activity of approximately 5–10 μCi/μg. Ten nM ligand is added to replicate tubes of 2.5×10$^5$ LS174T cells/tube, and incubated at 4° C. for one hour. Cells are washed twice with binding buffer and plated in 24 well plates. To some tubes a 200-fold molar excess of cold ligand is added to assess specific binding. To other tubes, 1 nM unlabeled rhIL-13 is added to assess effects on internalization and processing.

Supernatants are removed at multiple time points and brought to 10% TCA to precipitate intact the label, so as to distinguish label which dissociates versus label that is internalized, catabolized and released. Plates are washed three times with binding buffer. Cells are solubilized with 0.4 ml of 2 N NaOH for counting.

EXAMPLE 5

Biodistribution of Radiolabeled IL-13

Biodistribution of IL-13 is studied in CEA+ tumor-bearing nude mice, using the LS174T or HT-29 model systems. Five week old female nude mice are injected with 5×10$^6$ cells from the LS1747T or HT-29 cell lines, both of which are colon cancer cell lines, resulting in development of subcutaneous tumors. Biodistribution of $^{125}$I-IL-13 in mice simultaneously injected with $^{131}$I-labeled MN-14Fab' or MN-14scF$_v$, which have similar K$_d$s and MWs is compared.

Dual label biodistribution experiments using radioiodinated IL-13 with IL-4 and MN-14 Fab' as controls have been performed in both the LS174T and HT-29 tumor xenograft model systems to assess tumor and normal organ uptake of these agents. Uptake values observed were consistent with both the molecular mass of the agents and the level of expression of the corresponding binding proteins in the tumor (cognate receptor proteins for the cytokines and CEA for MN-14Fab'). In summary, IL-13 uptake in these colon tumors was typically in the range of 0.2–1.0 percent of injected dose/gram tissue (% ID/g), while the corresponding uptake values for MN-14Fab' were 4.0–7.5 for HT-29 and 7.0 to >20 for the LS174T tumors. The IL-4 control behaved similarily Il-13. These results are consistent with the low levels of cognate cytokine receptor in both of these tumors (as assessed by radiotracer binding to harvested tumor cells), the intermediate levles of CEA on HT-29 and the high levels of CEA on LS174T. Tumor uptake values were maximal for both cytokines and Fab' at 5 hours post-injection, which is consistent with their rapid clearance that is a consequence of their low molecular masses. Renal uptake of all agents was high and also peaked at 1–5 hours, which is consistent with the known renal clearance mechanism of such agents. Liver showed the highest uptake of IL-14 and IL-14 amongst other normal organs, which is consistent with the knowwn preclinical and clinical hepatotoxicity seen with higher doses of these agents.

A parallel set of experiments using the Ramos B cell tumor xenograft model were performed using radioiodinated IL-15, with IL-2 as cytokine control and LL2 Fab' (recognizing the CD22 B cell antigen) as their control. Overall results were similar in this model system, except that liver uptake values were lower with these cytokines compared to IL-13 and IL-14. These experiments confirmed the expected pharmacokinetic and pharmacodynamic behavior of the IL-4, IL-13, IL-2 and IL-15 cytokine agents. The results indicate that tumor uptake reflects the low basal lecvel of expression of the cognate cytokine receptors in both CEA+ carcinomas as well as lymphomas, which can be increased by first targeting tumors with antibody-Rα fusion proteins. Once targeted with this bifunctional agent, administration of armed, cognate cytokine is predicted to result in higher uptake than would occur with either the antibody or cytokine without pretargeting with the antibody-Rα agent.

EXAMPLE 6

Construction of a IL-13/Onconase Immunotoxin

A fusion protein consisting of IL-13 and onconase is genetically engineered following procedures outlined by Rybak for the production of mAb-onconase fusion proteins. *Tumor Targeting* 1: 141–147 (1995). Briefly, a sequence-confirmed fragment corresponding to the mature IL-13 protein is ligated to the sequence of onconase with the IL-13 sequence lying 5', though the other orientation also can be evaluated. Onconase genes are cloned from two or more frog species. Authentic fragments representing the fusion sequence are subcloned into the pET21d vector again using a C-terminal hexahistidine tag. The complete sequence encoding the entire IL-13-onconase fusion protein is confirmed in the pET vector in the XL1Blue strain as above. Appropriate clones are expanded to produce plasmid for transformation of the AD494 (DE3) *E. coli* expression strain.

Transformed clones are picked and grown in small scale culture, induced with IPTG, lysed in SDS sample buffer and separated on a SDS-PAGE gel for Coomassie staining and transblotting for detection both with anti-IL-13 antibodies and anti-onconase antibodies. Isolation and washing of inclusion bodies, their solubilization, renaturation and subsequent purification is performed using the steps outlined above. The final product is tested for its ability to bind the IL-13 receptor by labeling with $^{125}I$ and comparing it with equimolar concentrations of similarly labeled IL-13 in the cell binding assay described above. Conjugates with the ability to bind IL-13 are tested for cytotoxicity on cell lines known to express receptors for IL-13.

The conjugate is tested in the presence and absence of the sIL-13Rα-hMN-14scF$_v$ fusion protein to determine toxicity and the ability to bind and internalize greater amounts of the immunotoxin. A dose response curve for each experimental and control condition is generated.

EXAMPLE 7

Therapy of Colon, Lung, Breast, Pancreatic, Gastric Ovarian and Medullary Thyroid Carcinoma A patient having carcinoma of the colon, lung, pancreas, stomach, ovary, breast or medullary thyroid is infused intravenously with a sterile, pyrogen-free solution containing sIL-13Rα-hMN-14scF$_v$ fusion protein in phosphate-buffered saline (PBS), prepared according to Examples 1 and 2. Time is allowed for the fusion protein to bind to malignant tumor cells and to clear substantially from the circulation of the patient.

The patient then is infused intravenously on a predetermined schedule with a sterile, pyrogen-free solution that contains radioisotopically-labeled or drug-conjugated IL-13 or IL-13/onconase immunotoxin conjugate, prepared according to Example 6. Subsequent radiologic or radioimmunodetection methods are then used to evaluate antitumor responses.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications. For example, sIL-15Rα-Lym-2 scF$_v$ fusion protein can be constructed, expressed, purified and evaluated using similar methodology to that described for soluble IL-13Rα-MN-14scF$_v$ fusion protein in Examples 1 through 3. The cognate ligand for receptor moiety, IL-15, can be similarity armed or labeled with drug, toxin or radioniclide. In this case, the B-cell lines Ramos and RL can be used as the in vitro and preclinical mouse tumor xenograft model. The ultimate clinical malignancies that would be addressed are B and T cell lymphoma/leukemia, Hodgkin's disease and other HLA-DR+ cancers. This approach can also be used to suppress HLA-DR+ cell populations, which mediate immunologic or inflammatory diseases.

What is claimed is:

1. A targeting moiety comprising a conjugate of an antibody linked to a ligand-binding region of interleukin-13 receptor α subunit (IL-13Rα), which antibody is specific for carcinoembryonic antigen.

2. A targeting moiety as claimed in claim 1, comprising a covalent conjugate in which the antibody is covalently linked to the ligand-binding region.

3. A targeting moiety as claimed in claim 1, comprising a fusion protein of the antibody and the ligand-binding region.

4. A targeting moiety as claimed in claim 1, comprising a bispecific antibody that has a first specificity for carcinoembryonic antigen and a second specificity for IL-13Rα receptor subunit.

5. A composition comprising a targeting moiety according to claim 1, and a pharmaceutically acceptable carrier.

6. A kit comprising (i) a conjugate of interleukin-13 (IL-13) linked to a drug, radionuclide or toxin, and (ii) a targeting moiety comprising an antibody specific for a cellular antigen specific to a targeted cell, linked to the ligand-binding region of interleukin-13 receptor α subunit (IL13Rα).

7. A method of treatment for cancer, comprising:
first administering to a subject in need of such treatment a targeting moiety comprising a antibody specific for a cellular antigen specific to a targeted cell, linked to the ligand-binding region of interleukin-13 receptor α subunit (IL-13Rα) and then
administering to the subject a therapeutically effective amount of a conjugate of interleukin-13 (IL-13) linked to a drug, radionuclide or toxin.

8. A targeting moiety according to claim 1, wherein said antibody is an antibody fragment selected from the group consisting of F(ab')2, F(ab)$_2$, Fab', Fab, and Fv.

9. A targeting moiety according to claim 1, which is a hybrid antibody fragment that has two specificities.

10. A targeting moiety according to claim 1, wherein antibody is a single chain antibody scF$_v$.

11. A kit according to claim 6, wherein said antibody is an antibody fragment selected from the group consisting of F(ab')$_2$, F(ab)$_2$, Fab', Fab, and Fv.

12. A kit according to claim 6, wherein said antibody is a hybrid antibody fragment that has two specificities.

13. A targeting moiety according to claim 1, wherein said antibody is a single chain antibody scF$_v$.

* * * * *